United States Patent
Annangi et al.

(10) Patent No.: US 8,845,539 B2
(45) Date of Patent: Sep. 30, 2014

(54) METHODS AND SYSTEMS FOR ESTIMATING GESTATION AGE OF A FETUS

(75) Inventors: Pavan Kumar Veerabhadra Annangi, Bangalore (IN); Jyotirmoy Banerjee, Bangalore (IN); Dirk Ryan Padfield, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/328,479

(22) Filed: Dec. 16, 2011

(65) Prior Publication Data
US 2013/0158402 A1    Jun. 20, 2013

(30) Foreign Application Priority Data

Dec. 22, 2010    (IN) .......................... 3919/CHE/2010

(51) Int. Cl.
| | | |
|---|---|---|
| A61B 8/00 | (2006.01) | |
| A61B 5/103 | (2006.01) | |
| G06K 9/00 | (2006.01) | |
| A61B 8/08 | (2006.01) | |
| G06T 7/00 | (2006.01) | |

(52) U.S. Cl.
CPC .............. *A61B 8/0866* (2013.01); *A61B 8/5223* (2013.01); *A61B 8/0858* (2013.01); *A61B 8/0808* (2013.01); *A61B 8/488* (2013.01); *G06T 7/0012* (2013.01)
USPC ............ 600/443; 600/437; 600/588; 382/128

(58) Field of Classification Search
CPC .. A61B 8/0866; A61B 8/0858; A61B 8/0808; A61B 8/5223; A61B 8/488; G06T 7/0012
USPC .......... 600/437, 443, 449, 451, 588; 382/128, 382/131
See application file for complete search history.

(56) References Cited

U.S. PATENT DOCUMENTS

| | | | |
|---|---|---|---|
| 5,605,155 A | | 2/1997 | Chalana |
| 5,795,296 A | * | 8/1998 | Pathak et al. ................. 600/443 |
| 7,041,059 B2 | * | 5/2006 | Chalana et al. ............... 600/437 |
| 7,252,638 B2 | | 8/2007 | Kahn |
| 7,783,095 B2 | | 8/2010 | Carneiro |
| 7,995,820 B2 | * | 8/2011 | de Barros Carneiro et al. ............................. 382/128 |
| 2005/0004465 A1 | | 1/2005 | Abuhamad |
| 2008/0240532 A1 | | 10/2008 | Carneiro |

OTHER PUBLICATIONS

Hertzberg et al., "Third Ventricle : Size and Appearance in Normal Fetuses Through Gestation", Radiology, vol. 203, Issue 3, pp. 641-644, 1997.

Kalish et al., "Sonographic Determination of Gestational Age", Timisoara Medical Journal, vol. 59, Issue 2, 2009.

(Continued)

*Primary Examiner* — Michael Rozanski
(74) *Attorney, Agent, or Firm* — Global Patent Operation; Marc A. Vivenzio (57) ABSTRACT

Methods, systems and computer program products for estimating the gestational age of a fetus are provided. According to one embodiment, the method generates a component image from a segmented ultrasound image of a fetal head. The component image includes one or more edges. The method then identifies a third ventricle within the component image. The method estimates a length of a bi-parietal diameter, based at least in part on the orientation of the third ventricle. Thereafter, the method estimates the gestational age of the fetus.

10 Claims, 12 Drawing Sheets

(56) References Cited

OTHER PUBLICATIONS

Lu et al., "Fetal Head Detection and Measurement in Ultrasound Images by an Iterative Randomized Hough Transform", Medical Imaging, vol. 5370, pp. 557-565, May 12, 2004.

Marhaban et al., "Automatic Estimation of Gestational Age in Ultrasound Images Based on Direct Least-Squares Fitting of Ellipse", IEEJ Transactions on Electrical and Electronic Engineering, vol. 5, Issue 5, pp. 569-573, Sep. 2010.

Lu, Wei et al., "Automated Fetal Head Detection and Measurement in Ultrasound Images by Iterative Randomized Hough Transform", Uitrasound in Med. & Biol., vol. 31, No. 7, pp. 929-936, 2005.

Carneiro, G. et al., "Detection of Fetal Anatomies from Ultrasound Images Using a Constrained Probabilistic Boosting Tree", IEEE Transactions on Medical Imaging, vol. 27, No. 9., pp, 1342-1355, Sep. 2008.

Chalana, V. et al., "Automatic Fetal Head Measurements from Sonodraphic Images", Academic Radiology, vol. 3, No. 8., pp. 628-635, 1996.

Matsopoulos, G.K. et al., "Use of Morphological Image Processing Techniques for the Measurement of a Fetal Head from Ultrasound Images", Pattern Recognition, vol. 27, Issue 10, pp. 1317-1324, Oct. 1994.

Priestly, Shan B. et al., "Measurement of Bi-Parietal Diameter for Efficient Estimation of Fetal Age in The Second Trimester Using Dynamic Image Processing Algorithms", International Journal of Computational Intelligence Research, vol. 6, Issue 2, May 2010, p. 237-246.

\* cited by examiner

METHODS AND SYSTEMS FOR ESTIMATING GESTATION AGE OF A FETUS

BACKGROUND OF THE INVENTION

1. Field of the Invention

The present disclosure relates generally to ultrasound image processing and, more particularly, to estimating gestation age of a fetus from an ultrasound image.

2. Description of Related Art

Obstetric ultrasound imaging is used for a variety of purposes. Some of the information that can be monitored includes that of a fetal heart beat, malformations in the fetus, diagnosis and confirmation of early pregnancy, and the like. Further, measurements such as Crown-rump length, Femur length, abdominal circumference, Head Circumference (HC) and Bi-Parietal Diameter (BPD) can also be taken.

The length of the BPD can be used in assessing the gestational age of a fetus, especially during late first and second trimesters. The BPD length can be measured manually, using a caliper to read the distance on a fetal head image. This technique, however, can prove to be time consuming, cumbersome, and is prone to intra-observer and inter-observer variability.

Semi-automated and automated techniques for estimating the BPD length are also currently available. These techniques assume the fetal head to be an ellipse and then compute the BPD length as the length of the minor axis of the ellipse. A variety of approaches are used in the segmentation of the fetal head image as an ellipse. One such approach makes use of a semi-automated method in which the user marks a contour inside the fetal head. The contour is then used as an initialization to an active contour model which suitably inflates or deflates on the basis of an energy function.

According to another approach the fetal head is assumed to be elliptical and its parameters are estimated by means of iterative randomized Hough transform. Yet another approach utilizes pattern recognition techniques. In this approach, a set of training images, typically containing hundreds of images, having a labeled fetal head is used to train a probabilistic boosting tree. The fetal head image is then segmented and the BPD is computed based on the trained model.

The current approaches, however, do not consider the orientation of the BPD. This may lead to inaccurate measurements and visual quality of the BPD. For example, an error in estimating the BPD length by about 5% (~3 mm) may result in a deviation of estimated gestational age by one week in late second trimester.

Therefore, there is a need in the art for a method and a system for providing more accurate and reliable automated techniques to estimate the gestation age of the fetus from an ultrasound image.

BRIEF SUMMARY OF THE INVENTION

The above and other drawbacks/deficiencies may be overcome or alleviated by an embodiment of a method for estimating gestational age of a fetus. The method generates a component image from a segmented ultrasound in of the fetal head. The component image includes one or more edges. The method then identifies a third ventricle within the component image. Further, the method estimates the length of a Bi-Parietal Diameter (BPD) based on orientation of the third ventricle. Subsequently, the method estimates the gestational age of the fetus using the length of the BPD.

In one embodiment, an ultrasound imaging system is used for estimating gestational age of a fetus. The ultrasound imaging system includes one or more processors and a computer program code stored in a computer readable storage medium coupled to the one or more processors. The computer program code when executed causes the one or more processors to generate a component image from a segmented ultrasound image of a fetal head such that the component image includes one or more edges. Further, the computer program code further causes the one or more processors to identify a third ventricle within the component image. Subsequently, the computer program code further causes the one or more processors to estimate length of a Bi-Parietal Diameter (BPD) based upon orientation of the third ventricle.

In another embodiment, a computer program product including a non-transitory computer readable medium encoded with computer-executable instructions is used for estimating gestational age of a fetus. The computer-executable instructions when executed cause the one or more processors to generate a component image from a segmented ultrasound image of a fetal head. The component image comprises one or more edges. Upon execution the computer-executable instructions further cause the one or more processors to identify a third ventricle within the component image. Subsequently, the computer executable instructions, when executed, further cause the one or more processors to estimate length of a Bi-Parietal Diameter (BPD) based upon orientation of the third ventricle.

BRIEF DESCRIPTION OF THE. SEVERAL VIEWS OF THE DRAWINGS

These and other features, aspects, and advantages of the present system and techniques will become better understood when the following detailed description is read with reference to the accompanying drawings in which like characters represent like parts throughout the drawings, wherein.

DETAILED DESCRIPTION OF THE INVENTION

Figure 1:
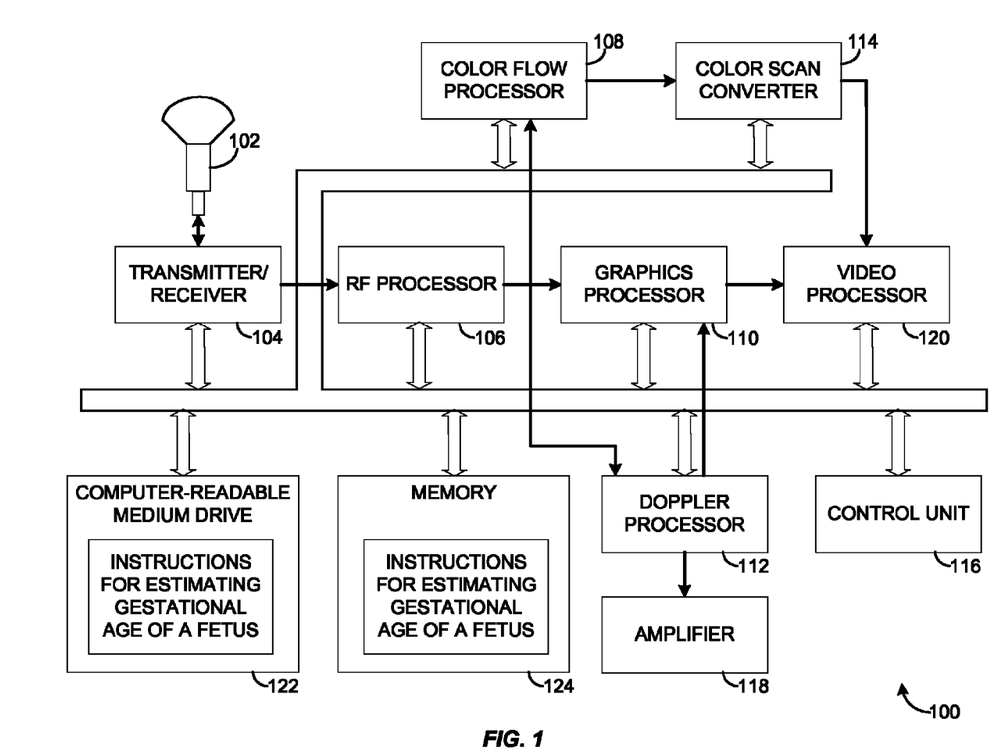
FIG. 1 is a schematic block diagram of an ultrasound imaging system for use in conjunction with various embodiments of the present system.

Referring to FIG. 1, major components of an exemplary ultrasound imaging system 100 benefiting from incorporating the present system are shown. The system 100 generally comprises a probe 102 which is connected to a transmitter/receiver circuitry 104. The transmitter/receiver circuitry 104 is designed so that the elements of the probe 102 will be fired at specified time intervals, with reflective pulses being detected using the probe 102 at another given time interval. The transmitter/receiver circuitry 104 is coupled to a control unit 116 via a bus. The control unit (or host computer) 116 controls circuitry in the system 100 via the bus. The control unit 116 is further coupled to a keyboard and a mouse, trackball or other device cursor control (not shown in FIG. 1) for movement and control information shown on a video display (not shown in FIG. 1) and for entering information and/or request to the control unit 116. The control unit 116 is coupled to a memory 124 and a computer-readable medium drive 122 via the bus, in an exemplary embodiment, the memory 124 and/or the computer-readable medium drive 122 includes instructions to estimate gestational age of a fetus.

Once a pulse is received by the transmitter/receiver circuitry 104, such information is transmitted to a radio frequency (RF) processor 106 for further processing. The radio frequency information (in-phase (I) and quadrature (Q) signals) is further transmitted to a graphics processor 110 and to a Doppler processor 112. Information generated by the Doppler processor 112 is transmitted to the graphics processor 110. The graphics processor 110 transmits scan line information to a video processor 120 for generation of black and white ultrasound information on the video display.

Such information may be transmitted in a suitable format, for example, National Television Standards Committee (NTSC) format. Further the information may be stored on a storage medium, such as, without limitation, a video tape, a compact disc (CD), a digital video disc (DVD), a removable storage drive, a Blu-ray disc and the like, for later clinical examination by attending medical personnel. In addition to information passed to the graphics processor 110 and the Doppler processor 112, the RF processor 106 transmits I and Q signals to a color flow processor 108. The color flow processor 108 is also controlled by the control unit 116 via the bus. The color flow processor 108 detects Doppler shift and blood flow information in living tissue, and thus transmits this information to a color scan converter 114. The color scan converter 114 interpolates point scan line information obtained from the color flow processor 108, and transmits that information to the video processor 120 which is responsible for processing the ultrasound image data.

A person of ordinary skill in the art will appreciate that the given ultrasound imaging system 100 is a generic outline of the major components present in the system without limiting the scope.

Figure 2:
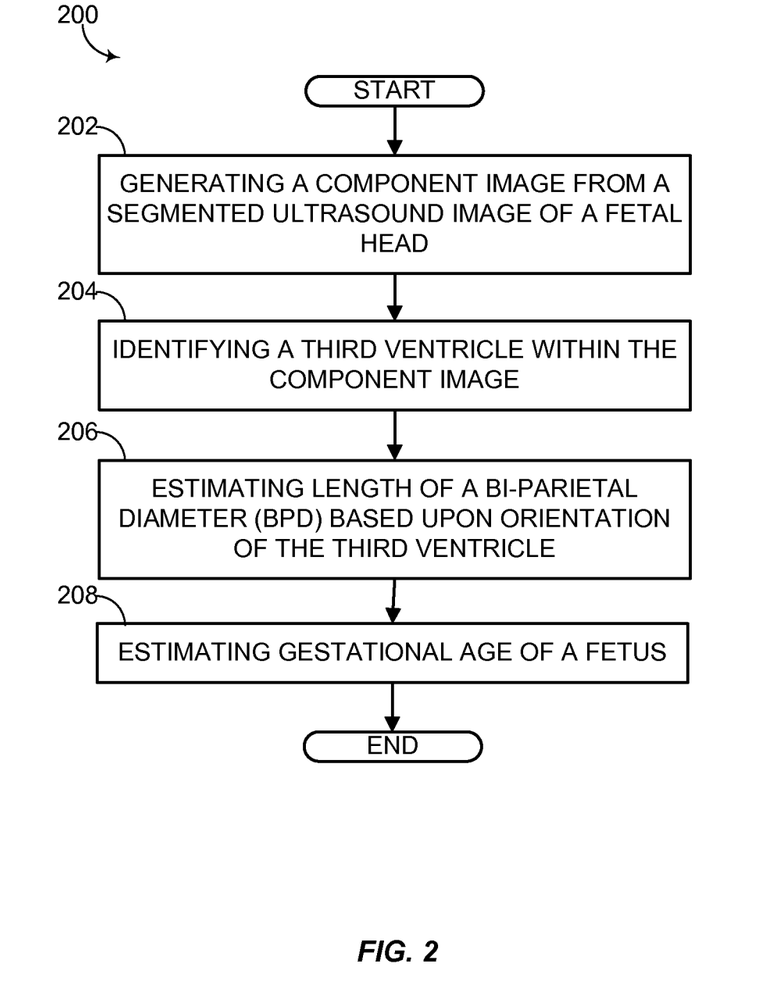
FIG. 2 is a flowchart illustrating an exemplary process of estimating gestational age of a fetus, in accordance with various embodiments.

FIG. 2 is a flowchart illustrating an exemplary process of estimating gestational age of the fetus, in accordance with various embodiments.

At step 202, the system 100 generates a component image from a segmented ultrasound image of a fetal head. The component image comprises one or more edges. Various embodiments for generating the component image are described in conjunction with FIG. 3.

The segmentation of the fetal head from the ultrasound image may be performed by any of the techniques known in the art. In one example implementation, one or more features having high curvature are extracted from the fetal head ultrasound image. Thereafter, a plurality of point set images are generated at multiple levels of diffusion. Finally, Random Sample Consensus (RANSAC) algorithm, in combination with the diffusion technique, is applied to the plurality of point set images to obtain the segmented fetal head.

At step 204, a third ventricle is identified within a segmented fetal head image. The identified third ventricle lies along a midline falx. An exemplary process for identifying the third ventricle is discussed in conjunction with FIG. 4.

Subsequently, the length of a bi-parietal diameter (BPD) is estimated, at step 206, based, at least in part, upon orientation of the identified third ventricle. In one embodiment, orientation of an Occipital Frontal Diameter (OFD) is delineated along the third ventricle. Thereafter, the orientation of the BPD in the segmented fetal head image is identified such that the BPD lies on the perpendicular bisector of the OFD. In an embodiment, the length of the BPD is measured from the beginning of a fetal cranium to the inside aspect of the distal fetal cranium at the level of a cavum septum pellucidium (CSP), also referred to as outer to inner BPD measurement. Further, in another embodiment, the outer to outer BPD measurement technique may be adopted, wherein the length of the BPD is measured from the beginning of the fetal cranium to the outer aspect of the distal fetal cranium.

According to additional embodiments, an average thickness of the fetal cranium is also estimated. The average thickness of the fetal cranium may then be used to estimate the BPD length. In one embodiment, fetal cranium components are extracted from the segmented fetal head image. The extracted fetal cranium components may then be skeletonized. Thereafter, the average thickness for the fetal cranium is computed based upon size of the extracted fetal cranium components and size of the skeletonized fetal cranium components. In one embodiment, the size of the extracted fetal cranium components and the skeletonized fetal cranium components is measured in terms of the number of pixels in respective components and the average thickness of the fetal cranium is computed as a ratio of the number of pixels in the extracted fetal cranium components to the number of pixels in the image obtained by an intersection operation between skeletonized fetal cranium components and the fetal cranium components.

Thereafter, the gestational age of the fetus is estimated using the length of the BPD at step 208. In an exemplary embodiment, the gestational age of the fetus may be estimated on the basis of a formula given as $$GA = 39.1 + 2.1 \text{ (len)} \qquad \text{Equation 1}$$

where:
GA=Gestational age in days
len=Length of the BPD in ram

In other embodiments the gestational age of the fetus may be estimated from any Standard Obstetric (OB) Tables, for example, HADLOCK tables, for the estimated length of the BPD.

Figure 3:
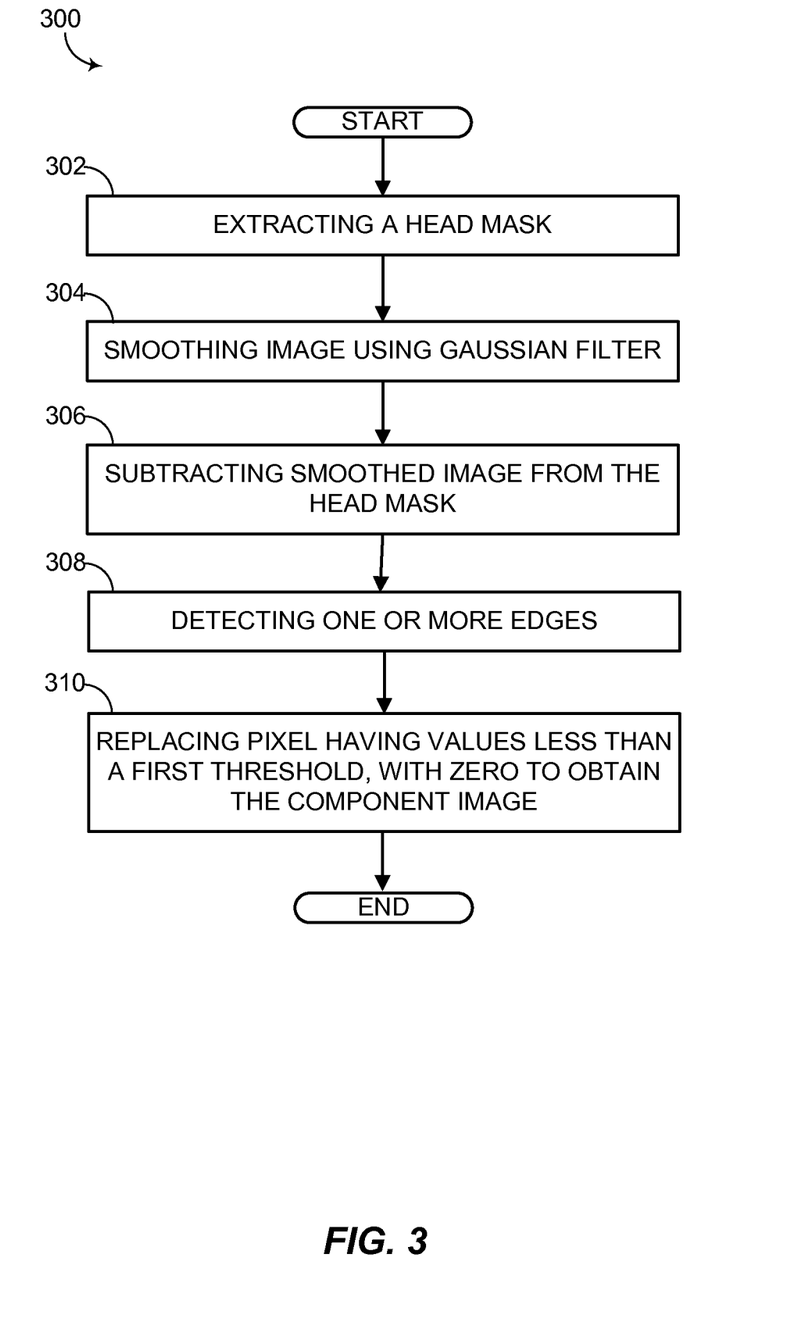
FIG. 3 is a flowchart illustrating an exemplary process of generating a component image, in accordance with various embodiments.

FIG. 3 is a flowchart illustrating an exemplary process of generating component image, in accordance with various embodiments.

At step 302, a head mask is extracted using known image processing techniques. At step 304, a smoothed image is generated. In one embodiment, the smoothening may he achieved by applying a Gaussian filter iteratively. A person of ordinary skill in the art will appreciate that other known techniques for smoothing the image may also be used without deviating from the spirit and scope of the present disclosure.

Thereafter, at step 306, the smoothed image is subtracted from the head mask obtained at step 302. This facilitates in enhancing one or more edges present in the head mask. At step 308, the one or more edges in the smoothed image are detected. In one embodiment, the one or more edges may he detected using Phase Congruency technique. Various other edge detection techniques, such as, without limitation, Frangi vesselness, curvature based thresholding, and the like may also be used for detecting the one or more edges.

At step 310, the component image is generated by replacing pixels having values less than a first threshold, with zero. In one embodiment, the first threshold is set to 10% of the maximum pixel value. A person of ordinary skill in the art will appreciate that the value of the first threshold is a design choice and any suitable value may be used.

A person of ordinary skill in the art will appreciate that the process, described herein, to generate the component image is merely an exemplary technique and does not limit the scope of the system. Other known solutions to obtain an image comprising one or more enhanced edges present in the segmented fetal head image may also he employed.

Figure 4:
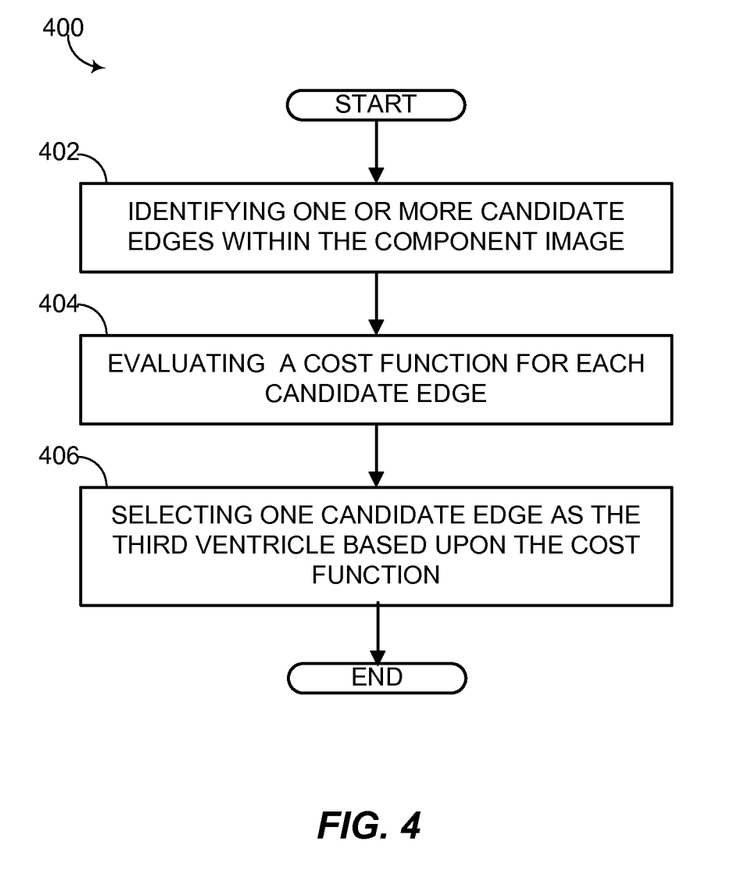
FIG. 4 is a flowchart illustrating an exemplary process for identifying the third ventricle, in accordance with various embodiments.

FIG. 4 is a flowchart illustrating an exemplary process for identifying the third ventricle, in accordance with various embodiments. At step 402, one or more candidate edges within the component image are identified. The one or more candidate edges may be identified based upon various parameters. For example, in one embodiment, the one or more candidate edges may be identified based upon size of the one or more edges. In another embodiment, distance of the one or more edges from a segmented fetal cranium may be used to identify the one or more candidate edges. In yet another embodiment, the one or more candidate edges may be identified using the size of the one or more edges and distance of the one or more edges from the segmented fetal cranium. Similarly, linearity of the one or more edges, orientation of the one or more edges, symmetry of the one or more edges with respect to the segmented fetal cranium, or combination thereof may be used to identify the one or more candidate edges. The parameters mentioned herein are for example purpose only and a person skilled in art will recognize any other parameters that may be used, instead of or in combination with the parameters described herein, to identify the one or more candidate edges.

Subsequently, at step 404, a cost function is evaluated for each candidate edge of the one or more candidate edges. In one embodiment, the cost function is based upon the size of the candidate edge and distance transform value of the candidate edge with respect to the segmented fetal head. According to one embodiment, the distance transform is computed with respect to the segmented fetal cranium. In alternate embodiment, the distance transform may be computed with respect to a center pixel of the segmented fetal head.

One exemplary cost function may be computed as a ratio of mean symmetry of a candidate edge from the segmented fetal cranium to the size of the candidate edge. According to one embodiment, the mean symmetry for the candidate edge may be defined as a summation of the closest Euclidean distance of each pixel in the candidate edge divided by the number of pixels in the candidate edge. In an alternate embodiment, the Euclidean distances of each pixel from the center pixel of the segmented fetal head may be used instead of the Euclidean distances from the segmented fetal cranium in the cost function The cost functions described herein are merely exemplary and any other suitable cost functions may be devised without deviating from the spirit and scope of the present system. Further, other suitable parameters may also be used, instead of or in addition to, the aforementioned parameters to design the cost function.

At step 406, one candidate of the candidate edges is selected as the third ventricle based upon the cost function. In one embodiment, the candidate edge with the minimum cost function is identified as the third ventricle within the component image.

Additionally, in an exemplary embodiment, an absence and/or under visualization of the third ventricle may be detected based upon the cost function. For example, if the smallest value of the cost function is more a threshold, it may be interpreted as an absent or under-visualized third ventricle.

In accordance with one embodiment, probabilistic Hough transform may be applied to at least one candidate edge of the one or more candidate edges. For example, the probabilistic Hough transform may be applied to candidate edges along the midline falx, according to one embodiment. This is advantageous in situations where the third ventricle may appear as a disjoint line. This may happen due to a variety of reasons, such as, fetal anomaly, incorrect scan plane acquisition, and the like. By applying the probabilistic Hough transform, the third ventricle may be identified more correctly. In accordance with another embodiment, the probabilistic Hough transform may be applied to the candidate edge that is identified as the third ventricle. This improves accuracy of identifying the third ventricle, especially in situations where a noise component may get attached to the third ventricle. The noise component may include any feature excluding the midline falx or any other disturbance present in the component image.

FIGS. 5-14 illustrate exemplary images corresponding to various steps involved in the processes described herein for the estimation of the gestation age, in accordance with various embodiments.

Figure 5:
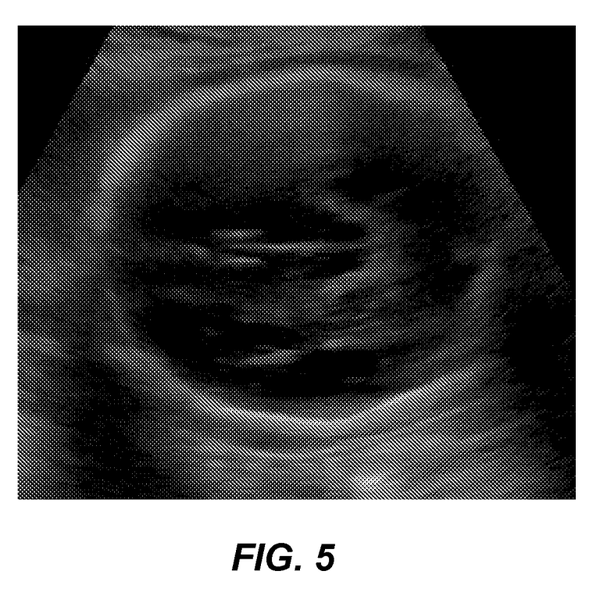
FIG. 5 illustrates an example ultrasound image of a fetal head, in accordance with various embodiments.

FIG. 5 illustrates an input ultrasound image of the fetal head, according to an exemplary embodiment. The ultrasound image of the fetal is then segmented using any of techniques known in the art, FIG. 6 illustrates an example image depicting segmented fetal head.

Figure 6:
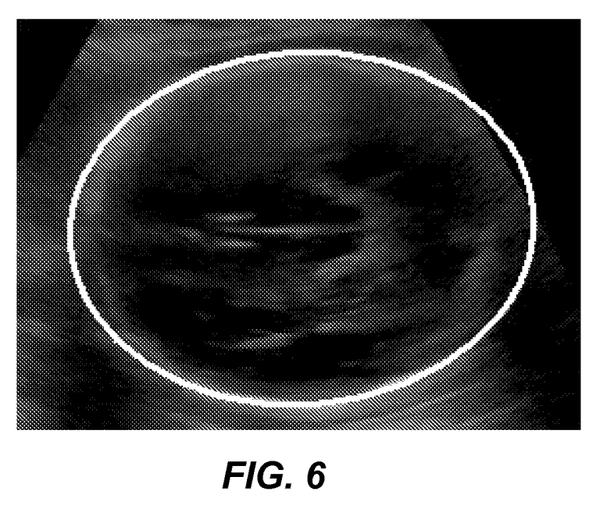
FIG. 6 illustrates an exemplary image showing segmented fetal head, in accordance with various embodiments.
Figure 7:
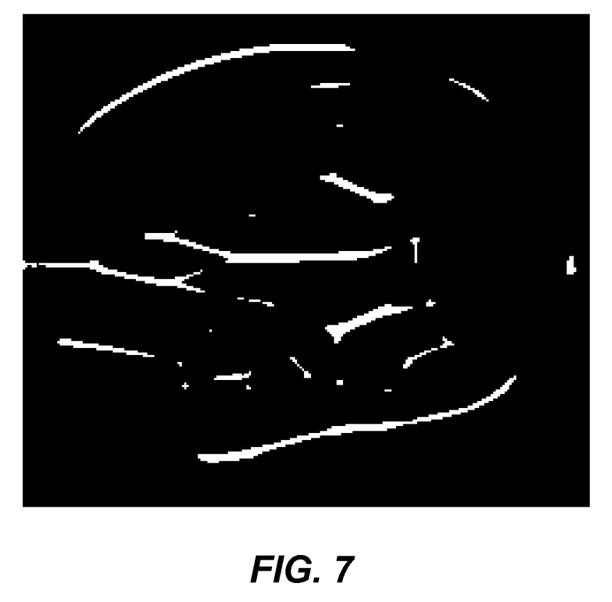
FIG. 7 illustrates an exemplary component image having one or more edges, in accordance with various embodiments.

FIG. 7 illustrates an example component image, having one or more edges, obtained from the segmented fetal head image depicted in FIG. 6. In this example case, the one or more edges are detected using the phase congruency technique.

Figure 8:
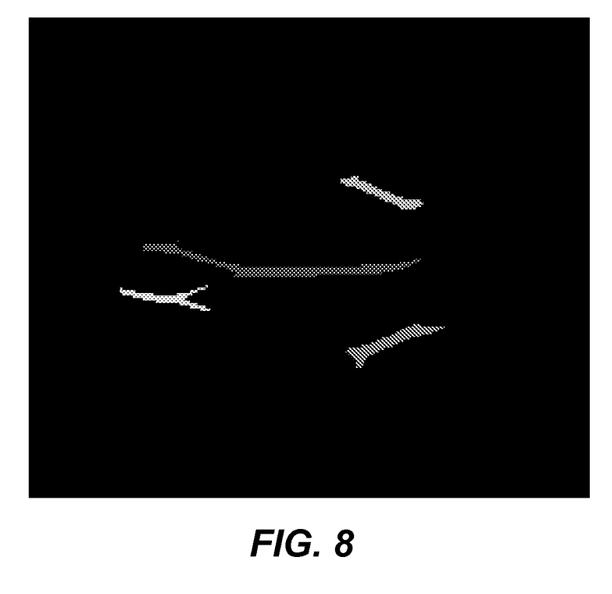
FIG. 8 illustrates an exemplary image having one or more candidate edges, in accordance with various embodiments.

As explained earlier, one or more candidate edges may be identified from the component image using various parameters. For example, the one or more candidate edges may be identified based on distance of the one or more edges from the segmented fetal cranium, linearity of the one or more edges, orientation of the one or more edges and the size of the one or more edges. FIG. 8 depicts one example component image containing one or more identified candidate edges.

Figure 9:
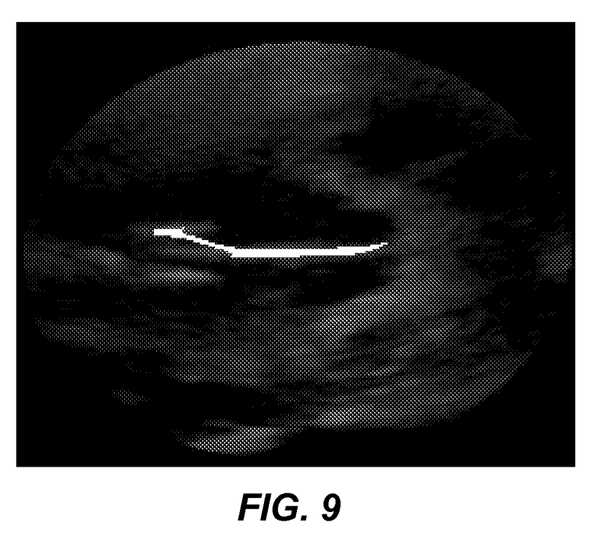
FIG. 9 illustrates an identified third ventricle within the component image, in accordance with various embodiments.
Figure 10:
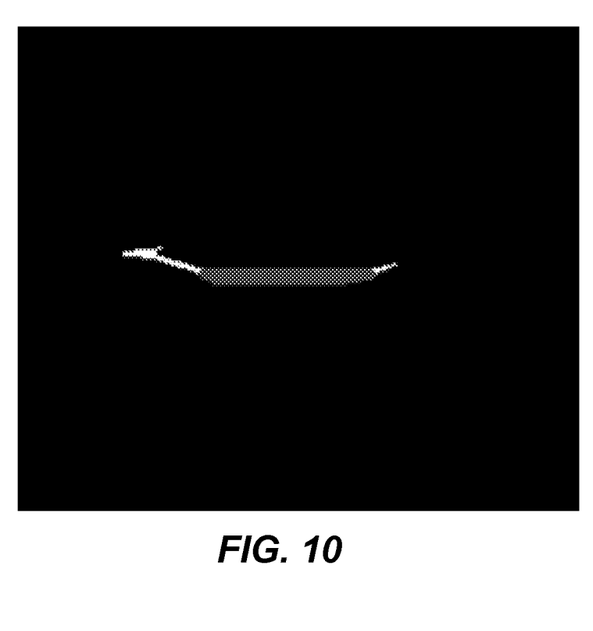
FIG. 10 illustrates an identified third ventricle within the component image after applying probabilistic Hough transform, in accordance with various embodiments.

A person of ordinary skill in the art will appreciate that the aforesaid approaches used for the candidate edge selection process may be used separately or in conjunction with a variety of other edge selection considerations, in order to identify the one or more candidate edges in the component image, The cost function is then evaluated for the one or more candidate edges. In this example, the cost function is computed as a ratio of mean symmetry of a candidate edge from the segmented fetal cranium to the size of the candidate edge. FIG. 9 illustrates a candidate edge having the lowest value of the cost function for the current example. From FIG. 9 it can be observed that the candidate edge includes the third ventricle and an attached noise component. Subsequently, probabilistic Hough transform is applied to the candidate edge to remove the noise component and the resultant edge is identified as the third ventricle as illustrated by a red line in FIG. 10.

Figure 11:
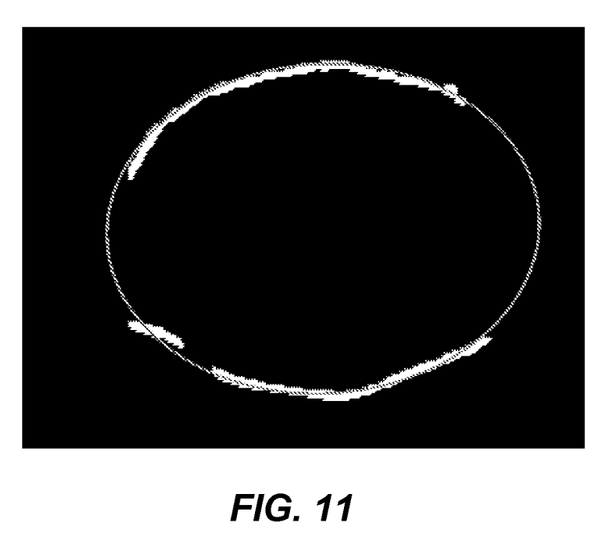
FIG. 11 illustrates an exemplary image having extracted fetal cranium components, in accordance with various embodiments.
Figure 12:
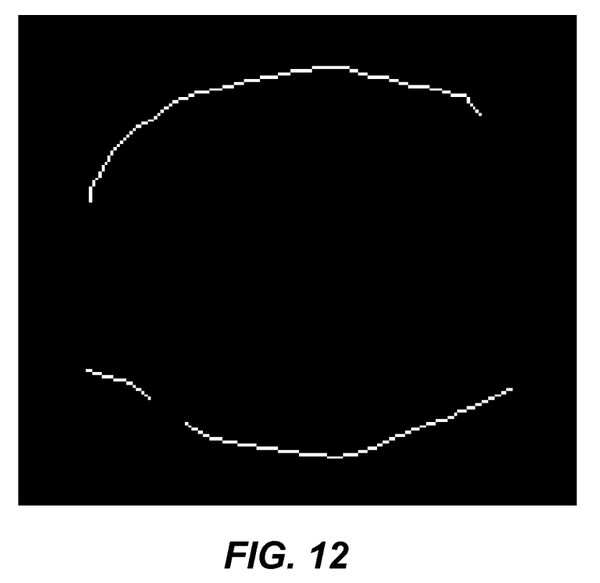
FIG. 12 illustrates an exemplary image having skeletonized fetal cranium components, in accordance with various embodiments.

As described herein, the average thickness of the segmented fetal cranium may also be determined according to various embodiments of the present system and techniques. The fetal cranium components are extracted from the ultrasound image. FIG. 11 illustrates the extracted fetal cranium components along with the segmented fetal head in the current example case. Thereafter, the extracted fetal cranium components are skeletonized as shown in FIG. 12. A ratio of the number of pixels in the extracted fetal cranium components to the number of pixels in the skeletonized fetal cranium components is computed to obtain the average fetal cranium thickness.

Figure 13:
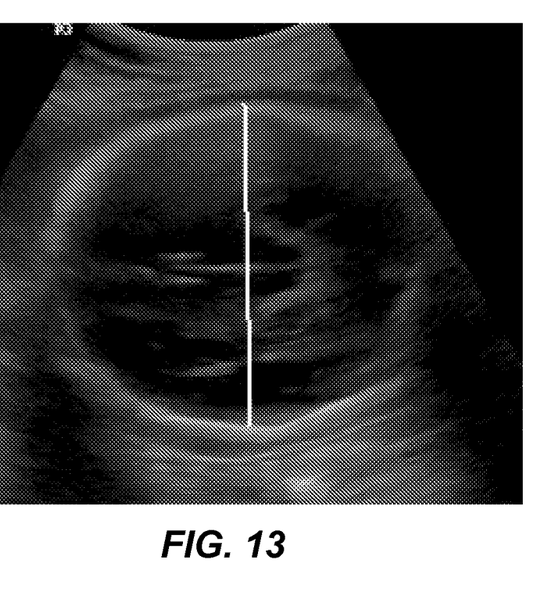
FIG. 13 illustrates a delineated BPD within the component image using the identified third ventricle according to outer-to-inner technique, in accordance with various embodiments.
Figure 14:
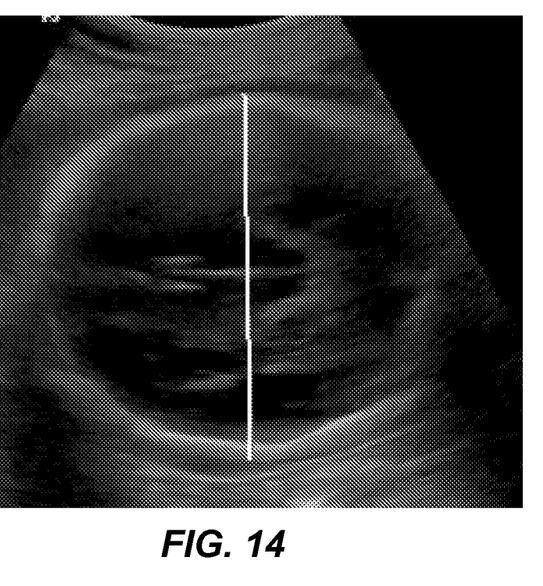
FIG. 14 illustrates a delineated BPD within the component image using the identified third ventricle according to outer-to-outer technique, in accordance with various embodiments.

Subsequently, the BPD is delineated based upon the orientation of the third ventricle. The orientation of the BPD in the component image is considered in the direction perpendicular to that of the identified third ventricle. Further, the length of the BPD is estimated. In one example, the length of the BPD is measured from the beginning of the fetal cranium to the inside aspect of the distal fetal cranium at the level of the CSP, also referred to as outer to inner BPD measurement. This is illustrated in FIG. 13. In another embodiment, the outer to outer BPD measurement technique may be adopted, wherein the length of the BPD is measured form the beginning of the fetal cranium to the outer aspect of the distal fetal cranium, as shown in FIG. 14.

Figure 15:
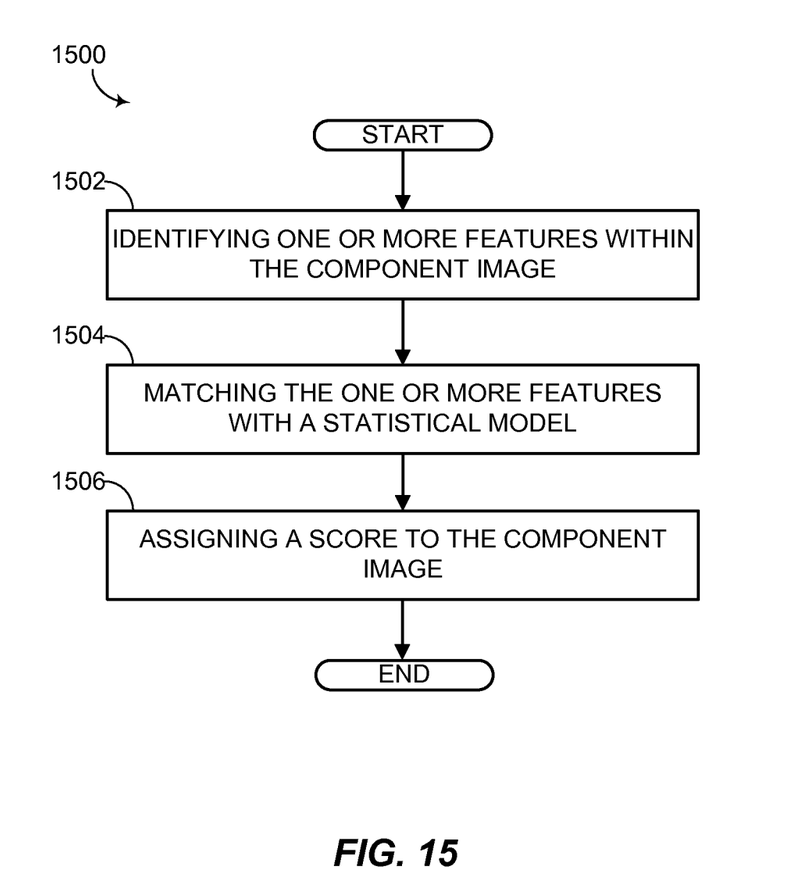
FIG. 15 is a flowchart illustrating an exemplary process for assigning a score to the component image, in accordance with various embodiments.

FIG. 15 is a flowchart illustrating an exemplary process 1500 for assigning a score to the component image. At step 1502, one or more features within the component image are identified. The one or more features may include, without limitation, a thalami, the CSP, the midline falx, and the like.

Subsequently, at step 1504, the one or more identified features are matched with a statistical model. In an exemplary embodiment, Active Appearance Model (AAM) is used as the statistical model, though any other suitable statistical model may be used.

At step 1506, the score is assigned to the component image based upon the matching. According to one embodiment, the score is indicative of the degree of similarity between the component image and a training dataset belonging to the statistical model. In various embodiments, the score may include a numerical value, a percentage, and the like. In additional embodiments, the score may be used to detect whether the third ventricle or other structures defined in a template image are present in the component image. For example, the template matching process provides a matching score for each structure, and any structure from the template with a score below a threshold can be flagged as not being present in the component image.

Figure 16:
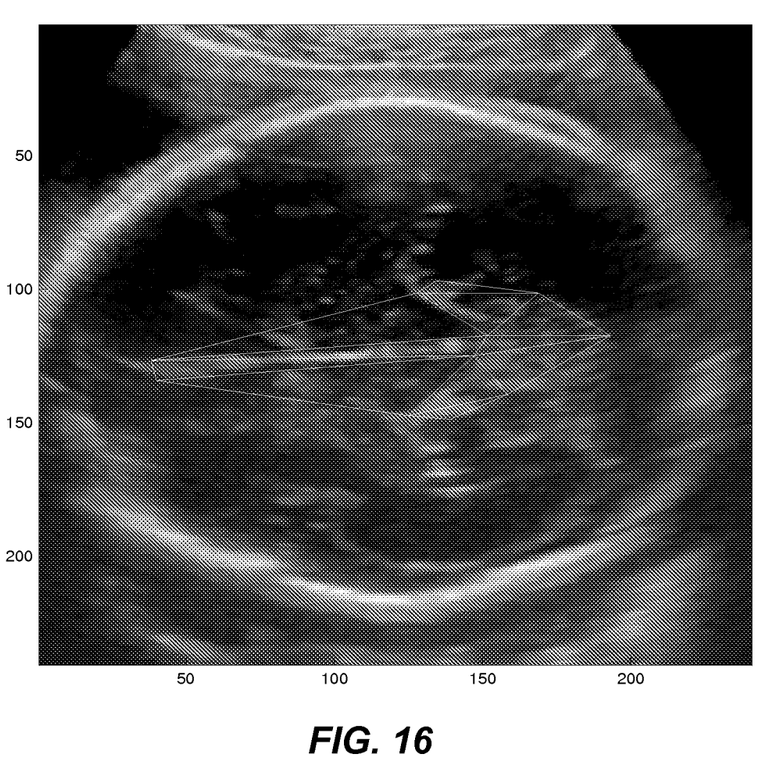
FIG. 16 illustrates a statistical model fitting approach, in accordance with various embodiments.

FIG. 16 illustrates an exemplary image showing results of such a statistical model fitting approach, according to one embodiment. In this example case, the one or more features for identification in a component image include a cavum septum pellucidium, thalami and third ventricle.

Figure 17:
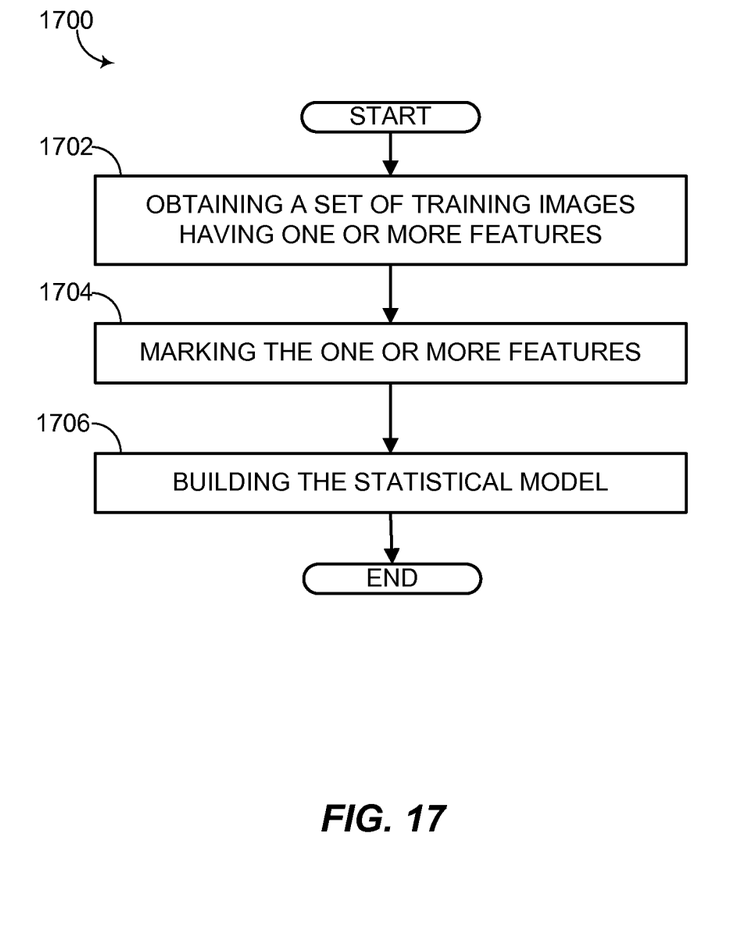
FIG. 17 is a flowchart illustrating an exemplary process for building a statistical model, in accordance with various embodiments.

FIG. 17 is a flowchart illustrating an exemplary process 1700 for building the statistical model. At step 1702, a set of training images are acquired to create the training dataset. Each training image includes the one or more features At step 1704, the one or more features are marked. The one or more features may include, without limitation, the CSP, the thalami, the midline falx, and the like. The features may be marked manually and/or by any known semi-automated or automated delineating technique.

At step 1706, the statistical model is built based on the one or more marked images. In one embodiment, iterative training of the statistical model may be performed. For example, first, a sample training dataset is acquired and the one or more features are marked. A rough estimation of the location of the one or more features is then established to provide a model. The model may be further refined by latching a new set of test images on to the model.

The methods disclosed herein can be embodied in the form of computer or controller implemented processes and apparatuses for practicing these processes. These methods can also be embodied in the form of computer program code containing instructions embodied in tangible media, such as floppy diskettes, CD-ROMs, hard drives, and the like, wherein, when the computer program code is loaded into and executed by a computer or controller, the computer becomes an apparatus for practicing the method. The methods may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the method. When implemented on a general-purpose microprocessor, the computer program code segments configure the microprocessor to create specific logic circuits.

While the systems and techniques have been described in considerable detail with reference to a few exemplary embodiments only, it will be appreciated that it is not intended to limit the invention to these embodiments only, since various modifications, omissions, additions and substitutions may be made to the disclosed embodiments without materially departing from the scope of the invention. In addition, many modifications may be made to adapt to a particular situation or an installation, without departing from the essential scope of the invention. Thus, it must be understood that the above invention has been described by way of illustration and not limitation. Accordingly, it is intended to cover all modifications, omissions, additions, substitutions or the like, which may be included within the scope and the spirit of the invention as defined by the claims.

What is claimed is:

1. A method for estimating gestational age of a fetus, the method comprising:
   generating a component image from a segmented ultrasound image of a fetal head, wherein the component image comprises one or more edges;
   identifying a third ventricle within the component image; and
   estimating length of a Bi-Parietal Diameter based, at least in part, upon orientation of the third ventricle.

2. The method of claim 1, wherein identifying the third ventricle comprises:

evaluating a cost function for one or more candidate edges within the component image; and selecting one candidate edge of the one or more candidate edges as the third ventricle based upon the values of the cost function.

3. The method of claim 2, wherein the cost function is based upon at least one of a size of a candidate edge and a distance transform value of the candidate edge with respect to the segmented fetal head.

4. The method of claim 2, wherein the one or more candidate edges are identified based upon at least one of size of the one or more edges, linearity of the one or more edges, orientation of the one or more edges, distance of the one or more edges from a segmented fetal cranium, and phase symmetry of the one or more edges with respect to the segmented fetal cranium.

5. The method of claim 2 further comprising applying probabilistic Hough transform on at least one candidate edge of the one or more candidate edges.

6. The method of claim 1 further comprising:

identifying one or more features within the component image;

matching the identified one or more features with a statistical model; and assigning a score to the component image based upon the matching.

7. An ultrasound imaging system for estimating gestational age of a fetus, the ultrasound imaging system comprising:

one or more processors configured to:

generate a component image from a segmented ultrasound image of a fetal head, wherein the component image comprises one or more edges;

identify a third ventricle within the component image; and estimate length of a Bi-Parietal Diameter based, at least in part, upon orientation of the third ventricle.

8. The ultrasound imaging system of claim 7, wherein the one or more processors are further configured to:

identify one or more features within the component image;

match the identified one or more features with a statistical model; and assign a score to the component image based upon the matching.

9. The ultrasound imaging system of claim 8, wherein the one or more processors are further configured to:

obtain a set of training images having the one or more features;

mark the one or more features in each training image of the set of training images; and build the statistical model based, at least part, upon the marked one or more features for the set of training images.

10. A computer program product comprising a non-transitory computer readable medium encoded with computer-executable instructions for estimating gestational age of a fetus, the computer-executable instructions, when executed, cause one or more processors to:

generate a component image from a segmented ultrasound image of a fetal head, wherein the component image comprises one or more edges;

identify a third ventricle within the component image; and estimate length of a Bi-Parietal Diameter based, at least in part, upon orientation of the third ventricle.

* * * * *

UNITED STATES PATENT AND TRADEMARK OFFICE
CERTIFICATE OF CORRECTION

| | | |
|---|---|---|
| PATENT NO. | : 8,845,539 B2 | Page 1 of 1 |
| APPLICATION NO. | : 13/328479 | |
| DATED | : September 30, 2014 | |
| INVENTOR(S) | : Annangi et al. | |

It is certified that error appears in the above-identified patent and that said Letters Patent is hereby corrected as shown below:

Specification

In Column 1, Line 59, delete "in of" and insert -- image of --, therefor.

In Column 2, Line 29, delete "OF THE." and insert -- OF THE --, therefor.

In Column 3, Line 36, delete "bus, in" and insert -- bus. In --, therefor.

In Column 4, Line 67, delete "ram" and insert -- mm --, therefor.

In Column 5, Line 6, delete "generating" and insert -- generating the --, therefor.

In Column 5, Line 10, delete "may he" and insert -- may be --, therefor.

In Column 5, Line 20, delete "may he" and insert -- may be --, therefor.

In Column 5, Line 36, delete "may also he" and insert -- may also be --, therefor.

In Column 6, Line 26, delete "more" and insert -- more than --, therefor.

In Column 6, Line 53, delete "art, FIG.6" and insert -- art. FIG.6 --, therefor.

In Column 7, Line 6, delete "image," and insert -- image. --, therefor.

In Column 7, Line 40, delete "measured form" and insert -- measured from --, therefor.

Signed and Sealed this
Twenty-seventh Day of October, 2015

Michelle K. Lee
*Director of the United States Patent and Trademark Office*